United States Patent [19]

Leong et al.

[11] Patent Number: 5,684,197

[45] Date of Patent: Nov. 4, 1997

[54] PROCESS FOR PREPARATION OF HYDRAZIDES

[75] Inventors: William Leong, Westfield, N.J.; Lyman Smith, Sterlilng, Va.

[73] Assignee: Schering Corporation, Kenilworth, N.J.

[21] Appl. No.: 766,442

[22] Filed: Dec. 12, 1996

[51] Int. Cl.$^6$ ............................................. C07C 241/04
[52] U.S. Cl. .......................... 564/151; 564/148; 564/149
[58] Field of Search .................................. 564/148, 149, 564/151

[56] References Cited

FOREIGN PATENT DOCUMENTS 9517407  6/1995  WIPO.

OTHER PUBLICATIONS

Alexakis et al., *J. Org. Chem.*, "Reactivity and Diastereoselectivity of Grignard Reagents," vol. 57, No. 17 (1992).

*Primary Examiner*—Peter O'Sullivan
*Attorney, Agent, or Firm*—Henry C. Jeanette

[57] ABSTRACT

A process for producing a hydrazide of the formula:

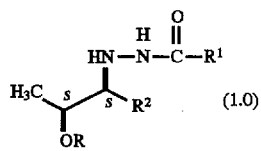

(1.0)

is disclosed. The process comprises reacting a hydrazone of the formula:

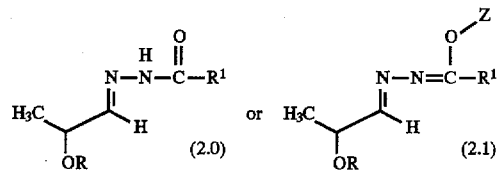

wherein said hydrazone is in toluene, with a mixture of Grignard reagents, wherein said Grignard reagents are in a suitable organic solvent; wherein: (A) Z is a suitable carbonyl protecting group; (B) R is a suitable —OH protecting group; (C) $R^1$ is selected from: H, a non-enolizable alkyl, a non-enolizable substituted alkyl, aryl, substituted aryl, —S-aryl, —S-(substituted aryl), —S-alkyl, —S-(substituted alkyl), alkoxy, substituted alkoxy, aryloxy, or substituted aryloxy; (D) said mixture of Grignard reagents comprises $R^2MgX$ in admixture with $R^3MgX$; (E) $R^2$ is a suitable alkyl, substituted alkyl, alkenyl, alkynyl, aryl, substituted aryl, or aralkyl group capable of adding to the —C=N group of the hydrazone to produce the hydrazide; (F) $R^3$ is a suitable alkyl, substituted alkyl, aryl or substituted aryl group that is more sterically hindered than said $R^2$ group; (G) X is independently selected from Cl, Br or I for each Grignard reagent; (H) when said hydrazone is a compound of Formula 2.0 then the reaction is conducted at a temperature of about +30° to about −40° C.; and (I) when said hydrazone is a compound of Formula 2.1 then the reaction is conducted at a temperature of about +40° to about −20° C.

20 Claims, No Drawings

PROCESS FOR PREPARATION OF HYDRAZIDES

BACKGROUND OF THE INVENTION

Alexakis et al., "Reactivity and Diastereoselectivity of Grignard Reagents toward the Hydrazone Functionality in Tolune Solvent", The Journal of Organic Chemistry, Volume 57, Number 17, pages 4563–4565 (Aug. 14, 1992) disclose that Grignard reagents, in toluene, display a strongly increased reactivity toward the hydrazone functionality. The results of a study of the reaction:

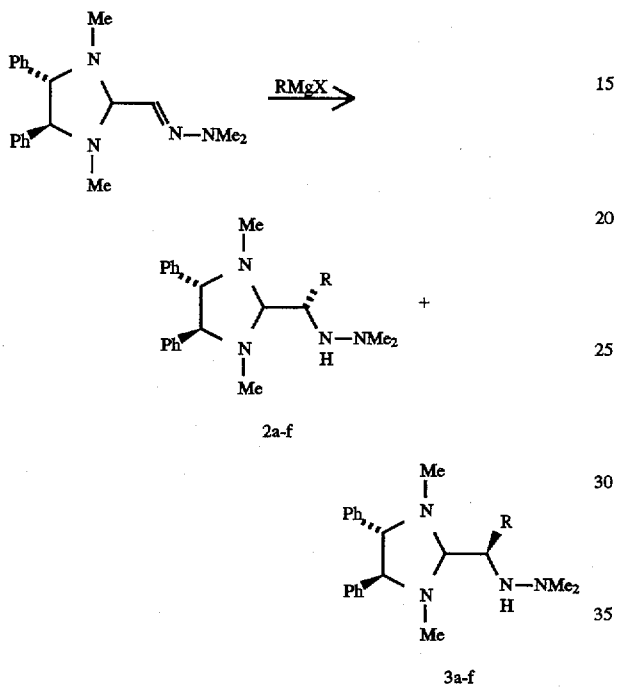

with various Grignard reagents in toluene is disclosed. However, the reactions involve the use of chiral auxiliaries to make enantiomers from dialkyl substituted hydrazones using an excess of Grignard reagent.

WO 95/17407, published Jun. 29, 1995, discloses antifungal compounds whose partial formula is:

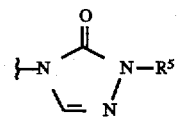

wherein $R^5$ can be, amongst others,

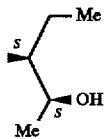

Scheme VI on page 35 describes a preparation of the antifungal compounds. In the reaction sequence an aldehyde (38) is reacted with $H_2NNHCHO$ in methanol to form the hydrazone (39). The hydrazone (39) is reacted with a Grignard reagent, e.g., ethylmagnesium bromide, in dry ether at a temperature of $-10°$ C. to room temperature to 24 hours to give the hydrazide (40) wherein the ratio of the S,S isomer: S,R isomer was 94:6. When the Grignard reaction is done in the presence of 1.2 equivalents of bis(trimethylsilyl) acetamide the SS to SR ratio was 99:1. The compounds referred to are disclosed in Scheme VI on page 27. It is believed that the N—NHCHO substituent in hydrazide (40) should be depicted with a single bond to the chiral center.

A process for producing diasteromers in high yield that uses less Grignard reagent, and tolerates the solvent that the Grignard reagent was prepared in (i.e., the process is not adversely effected by the solvent that the Grignard reagent was prepared in) would be a welcome contribution to the art. The invention described herein provides just such a contribution.

SUMMARY OF THE INVENTION

This invention provides a process for preparing a high diasteromeric yield of high purity of a hydrazide from a hydrazone. The hydrazides are useful as intermediates to antifungal compounds.

In the process, a hydrazone, preferably a hydrazone whose carbonyl group is protected, is reacted with a mixture of Grignard reagents to provide high yields of a specific diasteromer of the corresponding hydrazide. The mixture of Grignard reagents comprises a first Grignard reagent that will add the desired group to the substrate and a second Grignard reagent that is more sterically hindered (i.e., bulkier) than the first Grignard reagent.

Thus, this invention is directed to a process for preparing a hydrazide of the formula:

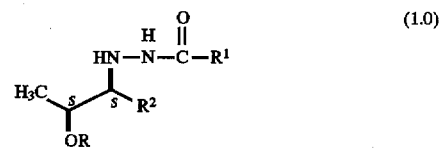
(1.0)

comprising reacting a hydrazone of the formula:

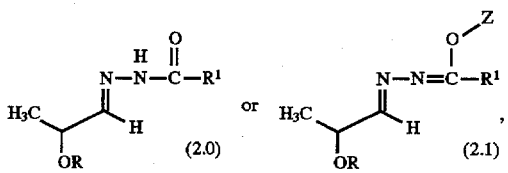

wherein said hydrazone is in toluene, with a mixture of Grignard reagents, wherein said Grignard reagents are in a suitable organic solvent; wherein:

(A) Z is a suitable carbonyl protecting group;

(B) R is a suitable —OH protecting group;

(C) $R^1$ is selected from: (1) H; (2) a non-enolizable alkyl; (3) a non-enolizable substituted alkyl; (4) aryl; (5) substituted aryl; (6)—S-aryl; (7)—S-(substituted aryl); (8)—S-alkyl; (9) —S-(substituted alkyl); (10) alkoxy; (11) substituted alkoxy (e.g., benzyloxy); (12) aryloxy (e.g., phenoxy); or (13) substituted aryloxy;

(D) said mixture of Grignard reagents comprises $R^2MgX$ in admixture with $R^3MgX$;

(E) $R^2$ is a suitable alkyl, substituted alkyl, alkenyl, alkynyl, aryl, substituted aryl, or aralkyl group capable of adding to the —C=N group of the hydrazone to produce the hydrazide;

(F) $R^3$ is a suitable alkyl, substituted alkyl, aryl or substituted aryl group that is more sterically hindered (i.e., bulkier) than said $R^2$ group;

(G) X is independently selected from Cl, Br or I for each Grignard reagent;

(H) when said hydrazone is a compound of Formula 2.0 then the reaction is conducted at a temperature of about +30° to about −40° C.; and (I) when said hydrazone is a compound of Formula 2.1 then the reaction is conducted at a temperature of about +40° to about −20° C.

DETAILED DESCRIPTION OF THE INVENTION

As used herein, the following terms have the following meanings, unless defined otherwise:

alkenyl—represents straight and branched carbon chains having at least one carbon to carbon double bond and containing from 2 to 12 carbon atoms, preferably from 2 to 6 carbon atoms;

alkyl—(including the alkyl portion of alkoxy and aralkyl) represents straight or branched carbon chains having from 1 to 20 carbons and preferably from 1 to 6 carbons;

alkynyl—represents straight and branched carbon chains having at least one carbon to carbon triple bond and containing from 2 to 12 carbon atoms, preferably from 2 to 6 carbon atoms;

aralkyl—represents an aryl group (as defined below) bound to an alkyl group (as defined above) such as benzyl;

aryl—(including the aryl portion of aryloxy and aralkyl) represents a carbocyclic aromatic group containing from 6 to 15 carbon atoms and having at least one aromatic ring, such as phenyl or naphthyl, with all substitutable carbons of the carbocyclic group being optionally substituted with one or more groups selected from halo, alkyl, hydroxy, alkoxy, phenoxy, —$CF_3$, amino, alkylamino, dialkylamino or $NO_2$, for example said aryl group is optionally substituted with 1 to 3 of the above mentioned groups; those skilled in the art will appreciate that only halo substituents which do not interfer with the formation of the Grignard reagents are selected for the substituted aryl $R^2$ groups;

BOM—represents benzyloxymethyl;

Bu$^t$ or t-Bu—represents tertiary butyl (—$C(CH_3)_3$);

carbonyl (—C=O) protecting group—represents a protecting group which blocks a —C=O group by binding to the oxygen atom to produce a —C—O-Z group, thereby preventing reactions involving the —C=O group from occurring during the process of the invention; carbonyl protecting groups are well known in the art and methods for the formation and removal of carbonyl protecting groups are also well known, such as those described in Greene, et al., "Protective Groups in Organic Synthesis", 2nd ed., pages 175 to 223, John Wiley & Sons (New York 1991);

EtOAc—represents ethyl acetate;

halo—represents a fluoro, chloro, bromo or iodo group;

hydroxyl or hydroxy (—OH) protecting group—represents a protecting group which blocks an —OH group thereby preventing reactions involving the —OH group from occurring during the process of the invention; hydroxyl protecting groups are well known in the art and methods for the formation and removal of hydroxyl protecting groups are also well known, such as those described in Greene, et al., "Protective Groups in Organic Synthesis", 2nd ed., pages 10–144, John Wiley & Sons (New York 1991);

MOM—represents methoxymethyl;

non-enolizable alkyl or substituted alkyl—represents an alkyl group or substituted alkyl group that does not have an acidic hydrogen on the carbon bound to the carbonyl carbon of the hydrazone thereby preventing enolization;

Red-Al—represents sodium bis(2-methoxyethoxy) aluminum hydride;

substituted alkyl—represents an alkyl group having 1 to 3 substituents selected from halo, $C_1$–$C_6$ alkoxy, aryl or aryloxy;

substituted aryl—represents an aryl group having 1 to 3 substituents selected from halo, alkyl, or $C_1$–$C_6$ alkoxy;

TBME—represents tert-butyl methyl ether;

TBDMS—represents tert-butyl dimethylsilyl—i.e.,

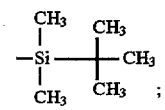

TMS—represents trimethylsilyl;

THF—represents tetrahydrofuran; and

THP—represents tetrahydropyranyl.

The reaction of the hydrazone (2.0 or 2.1) with the mixture of Grignard reagents is preferably done under an inert atmosphere, such as nitrogen. Preferably, hydrazone 2.1 is used. The hydrazone is in an amount of toluene that effectively allows the admixture of the reactants.

Suitable organic solvents for the Grignard reagents are selected from toluene, THF, diethyl ether, TBME or mixtures thereof. Preferably, THF, diethyl ether or TBME is used.

Suitable carbonyl protecting groups (Z) include but are not limited to: $C_1$ to $C_6$ alkyl (e.g., methyl or ethyl), trimethylsilyl, triethylsilyl, triisopropylsilyl, dimethylthexylsilyl, acyl ($CH_3C(O)$—), and —$OP(OR^4)_2$ wherein each $R^4$ is the same alkyl group (e.g. ethyl), or each $R^4$ is the same aryl group (e.g., phenyl).

The reaction of the hydrazone of Formula 2.0 or 2.1 with the mixture of Grignard reagents is conducted at a temperature which allows the reaction to proceed at a reasonable rate without the formation of unwanted by-products. Hydrazones whose carbonyl groups are protected, i.e., compounds of Formula 2.1, can be reacted with the mixture of Grignard reagents at a higher temperature than the unprotected hydrazones of Formula 2.0. Those skilled in the art will appreciate that usually the hydrazone solution is cooled to a low temperature before the mixture of Grignard reagents is added to the solution. After addition, the resulting reaction mixture is allowed to react at a temperature that is usually higher than the addition temperature of the Grignard reagents.

When the carbonyl group of the hydrazone is unprotected, i.e., a compound of Formula 2.0, the reaction temperature is about +30° to about −40° C., with about 0° to about −15° C. being preferred, and about 0° to about −5° C. being most preferred. Usually, the hydrazone solution is cooled to the lower end of the temperature range, e.g., about −20° C., in preparation for the addition of the Grignard reagents, the temperature is maintained at a higher temperature, e.g., about −5° C., during the addition of the Grignard reagents, and then the reaction is allowed to proceed at a higher temperature, e.g., about 0° C., to completion.

When a protected hydrazone is used, i.e., a compound of formula 2.1, the reaction temperature is about +40° to about −20° C., with about 0° to about +25° C. being preferred, about 10° to about 25° C. being more preferred, and about 25° C. being most preferred. Usually, the hydrazone solution is cooled to the lower end of the temperature range, e.g., about 0° C., in preparation for the addition of the Grignard reagents, the temperature is maintained at a higher temperature, e.g., below about +5° C., during the addition of the Grignard reagents, and then the reaction is allowed to proceed at a higher temperature, e.g., room temperature, to completion.

Representative hydroxyl protecting groups, i.e., substituent R, include but are not limited to $C_1$ to $C_8$ alkyl, phenyl (—$C_6H_5$), benzyl (—$CH_2C_6H_5$), allyl, BOM, MOM, TMS, TBDMS, and THP. Preferably, benzyl is used.

Preferably, $R^1$ is H.

Suitable non-enolizable groups for $R^1$ include but are not limited to: (1) —$C(Cl)_2$-alkyl; and (2) $C_3$ to $C_8$ secondary alkyl groups such as —$CH(CH_3)CH_2CH_3$ (s-$C_4H_9$) or —$CH(CH_3)_2$; (2) $C_3$ to $C_8$ tertiary alkyl groups such as —$C(CH_3)_2CH_2CH_3$, t-$C_4H_9$, —$C(C_6H_5)(CH_3)_2$ and —$C(C_6H_5)_3$.

Representative examples of $R^1$ also —$OC(CH_3)_3$, —$OCH_2C_6H_5$ (benzyloxy), phenoxy, S—$CH_3$, S—$C_2H_5$, and —$SC_6H_5$. Of these groups —$OC(CH_3)_3$ is preferred.

The mixture of Grignard reagents comprises $R^2MgX$ in admixture with $R^3MgX$. Any group capable of adding to the carbonyl group of an aldehyde or ketone in a Grignard reaction is a suitable $R^2$ group for addition to the —C=N— group of the hydrazone. Preferably, $R^2$ is a 1°, 2° or 3° alkyl group, more preferably a $C_1$ to $C_8$ alkyl group, even more preferably a 1° alkyl group, and most preferably ethyl. Other examples of suitable $R^2$ groups include but are not limited to: methyl; (n- or s-)propyl; (n-, s-, or t-)butyl; (n-, s-, or t-)pentyl; (n-, s-, or t-)hexyl; (n-, s-, or t-)heptyl; (n-, s-, or t-)octyl; vinyl; —$CH_2CH=CH_2$ (allyl); ethynyl; phenyl; and benzyl.

$R^3$ is any suitable group capable of forming a Grignard reagent wherein said group is more sterically hindered than the $R^2$ group. Thus, $R^3$ can be selected from the same groups defined for $R^2$ provided that the group selected for $R^3$ is more sterically hindered than the $R^2$ group. For example, when $R^2$ is ethyl then $R^3$ can be selected from: (s- or t-)butyl, (s- or t-)pentyl, (s- or t-)hexyl, or (s- or t-)octyl, with a t-alkyl group being preferred, and t-butyl being most preferred.

X represents a halogen atom selected from Cl, Br or I, with Cl or Br being preferred.

The individual Grignard reagents are known in the art or can be readily made by known techniques.

The $R^2MgX$ Grignard reagent is used in a sufficient amount to effectively introduce the $R^2$ group into all or substantially all of the substrate (i.e., Formula 2.0 or 2.1). Generally, the $R^2MgX$ Grignard reagent is used in an amount of at least about 1.0 equivalent (eq) based on the hydrazone 2.0 or 2.1. Usually, for the hydrazone 2.0, the $R^2MgX$ Grignard reagent is used in amounts of about 1.0 to about 4.0 eq, with about 2.0 to about 3.0 eq being preferred, and about 2.0 to about 2.4 eq being most preferred. Usually, for the hydrazone 2.1, the $R^2MgX$ Grignard reagent is used in amounts of about 1.0 to about 1.5 eq, with about 1.0 to about 1.3 eq being preferred, and about 1.1 to about 1.2 eq being most preferred.

The $R^3MgX$ Grignard reagent is used in a sufficient amount to facilitate the addition of the $R^2$ group to produce the desired diasteromer in high yield. The $R^3MgX$ Grignard reagent can be used in an excess, relative to the amount of the $R^2MgX$ Grignard reagent, which excess is not great enough to cause the addition of the $R^3$ group to the substrate.

Generally, the $R^3MgX$ Grignard reagent is used in an amount that is at least about 0.5 times the amount of the $R^2MgX$ Grignard reagent, with at least about one times the amount being preferred, about 1 to about 10 times being more preferred, about 1 to about 2 times being even more preferred, and about one times the amount being most preferred. Thus, it is most preferred that the ratio of $R^2MgX$ to $R^3MgX$ be about 1:1.

The starting reactant of Formula 2.0 or 2.1 can be made according to techniques known in the art. For example, compounds of Formula 2.0, wherein $R^1$ is H can be made according to the technique disclosed in WO 95/17407 published on Jun. 29, 1995, the disclosure of which is incorporated herein by reference thereto. By using techniques known in the art, compounds of Formula 2.0 wherein $R^1$ is other than H and/or R is other than benzyl can be made by using the appropriate hydrazone and/or the appropriate —OH protecting group, respectively. Similarily, compounds of Formula 2.1 can be made by selecting the appropriate carbonyl protecting group and the appropriate —OH protecting group.

The benzyloxyamide (5.0) used in the examples can be prepared according to methods known in the art. For example, by the reaction:

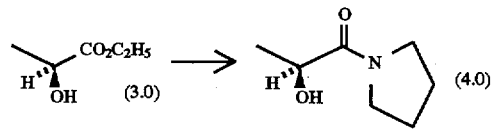

the chiral hydroxy amide (4.0) can be prepared from ethyl (S)-lactate (3.0) via substantially the same procedure as described in Kobayashi et al., Bull. Chem Soc. Jpn., 62, 3038–3040 (1989).

Then, by the reaction:

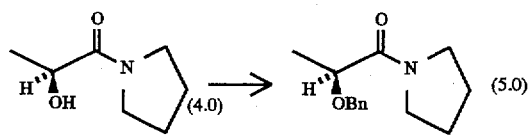

the hydroxy amide (4.0) can be converted to the corresponding benzyl ether (5.0 wherein Bn represents benzyl) via procedures such as the one described in Kobayashi et al., above. Alternatively, benzylation can be carried out via other methods known in the art such as those described in Greene et al., "Protective Groups in Organic Synthesis", 2nd Edition, pages 47–49, John Wiley & Son, New York (1991).

The examples that follow are intended to exemplify the claimed invention, and such examples should not be construed as limiting the disclosure or the claimed invention.

PREPARATION 1

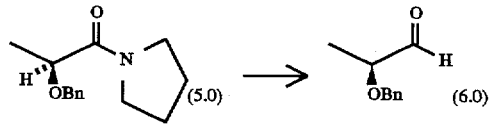

Into a round bottom flask equipped with a mechanical stirrer was placed 5.0 (58.32 g) and toluene (250 mL). The mixture was stirred until 5.0 was dissolved and then cooled to −10° to −5° C. To this solution was dropwise added a solution of Red-Al in toluene (44.1 mL, 3.4M in toluene)

over a period of 30 minutes (while maintaining the reaction temperature below −5° C.). The reaction was stirred for 8–12 hours at 0° C. while monitoring the progress by HPLC. Upon completion, the reaction was quenched with isopropanol (10 mL) at 0° C., stirred for 30 minutes, and then the resulting mixture was poured into 2N HCl (300 mL). The mixture was stirred to ensure dissolution of aluminium salts and the layers were separated. The aqueous phase was extracted with EtOAc (100 mL×3). The combined organic layers were washed successively with water (100 mL), saturaterd aqueous NaHCO₃, brine and dried (MgSO₄). The volatile solvents were removed under vacuo to yield 36.9 g of 6.0 as an oil. MS m/z 165 (M+1).

PREPARATION 2

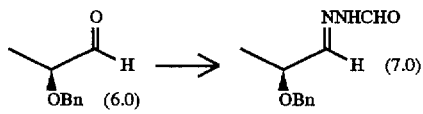

Into a round bottom flask equipped with a mechanical stirrer was placed formic hydrazide (25.23 g) and hexane (400 mL) at room temperature. To this suspension was added a solution of aldehyde 6.0 in hexane (65.7 g in 200 mL hexane) and the solution was stirred for about 24 hours at room temperature (r.t.). The resulting mixture was partitioned into cold water (300 mL) and EtOAc (100 mL), and the layers were separated. The aqueous phase was extracted with EtOAc (100 mL×4). The combined organic layers were washed with water (100 mL) and dried (MgSO₄). The volatile solvents were removed under vacuo to yield 74.91 g of an oil which solidified on standing. The solid was purified by crystallization from minimal 3% TBME in hexane (about 450 mL) and gentle heating. The white crystals thus formed were cooled to 0° C., filtered and dried in a draft vacuum chamber (r.t.) to afford 66.5 g ( 81% yield) of hydrazone 7.0 as a white solid. MS m/z 207.0 (M+1).

PREPARATION 3

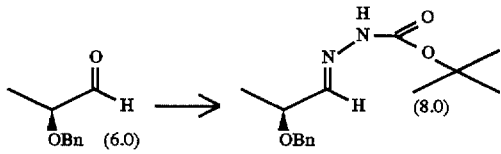

Into a round bottom flask equipped with a mechanical stirrer was placed t-butyl carbazate (1.38 g) and hexane (10 mL) at room temperature. To this suspension was added a solution of aldehyde 6.0 in hexane (1.64 g in 10 mL hexane) and the solution was stirred for about 24 hours at room temperature. The resulting mixture was partitioned into cold water (15 mL) and stirred for 30 minutes at room temperature. The solids that formed were filtered and dried in a draft vacuum chamber (r.t. for about 16 hours) to afford 2.49 g (90% yield) of hydrazone 8.0 as a white crystalline needle.

PREPARATION 4

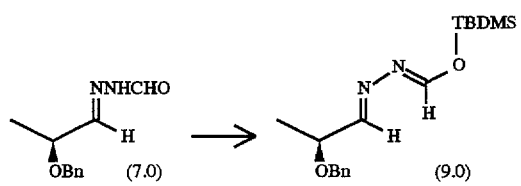

Into a round bottom flask equipped with a mechanical stirrer was placed 7.0 (61.89 g) and TBME (600 mL) at room temperature. To this solution at room temperature was added methylamine (63.0 ml), followed by TBDMS-Cl (49.74 g), and the solution was stirred for about 24 hours at room temperature. The resulting mixture was filtered through a pad of celite and concentrated in vacuo to an oil. This oil was dissolved in TBME (100 mL) and filtered through a pad of celite. The solution was concentrated in vacuo to afford an oil. The oil thus obtained weighed 91.0 g (95%). Proton NMR showed 97% of silylated hydrazone. MS m/z 207.1 ([M-TBDMS]+1). This oil was not purified.

EXAMPLE 1

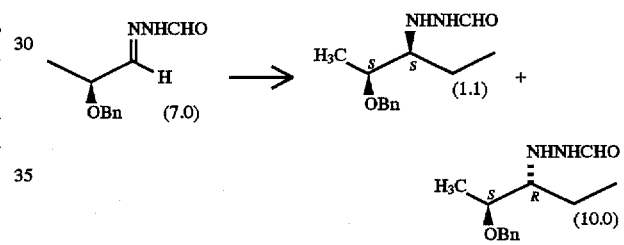

Into a round bottom flask equipped with a stirrer, and under a nitrogen atmosphere, was charged ethylmagnesium chloride (176 mL, 352 mmol, 2.0M in THF) at room temperature (24°–28° C.). To this was charged t-butylmagnesium chloride (469 mL, 352 mmol, 0.74M in THF) and the solution was stirred at room temperature. The resulting solution is approximately 0.6M in "ethyl" concentration.

Into a separate round bottom flask equipped with a stirrer and an addition funnel, and under a nitrogen atmosphere, was placed hydrazone 7.0 (33.0 g) and toluene (480 mL) at room temperature. This solution was cooled to −20° C. and was treated to a dropwise addition of the Grignard reagent (the temperature was maintained below −5° C). Upon addition, the reaction mixture was stirred at 0° C. for about 24 hours. The reaction was monitored for completion by HPLC. The resulting mixture was quenched by pouring into 2 L of ice-water and extracted with TBME (500 mlx3). The organic layers were washed with saturated aqueous NaCl and dried (MgSO₄). The volatile solvents were removed under vacuo to field 37.5 g of an oil. HPLC assay indicated the field to be 63% pure 1.1 with an SS:SR ratio (1.1:10.0) of 97:3. MS m/z 259.1 (M+1).

EXAMPLE 2

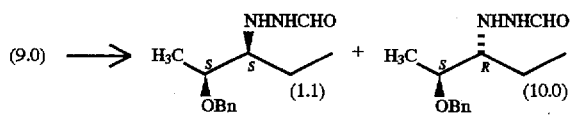

Into a round bottom flask equipped with a stirrer, and under an inert atmosphere was charged ethylmagnesium chloride (157.6 mL, 315 mmol, 2.0M in THF) at room temperature (24°–28° C.). To this was charged t-butylmagnesium chloride (370 mL, 315 mmol, 0.85M in THF) and the solution was stirred at room temperature. The resulting solution was approximately 0.597M in "ethyl" concentration.

Into a separate round bottom flask equipped with a stirrer and an addition funnel, and under a nitrogen atmosphere, was placed TDBMS-hydrazone 9.0 (89.73 g) and toluene (420 mL) at room temperature. This solution was cooled to 0° C. and was treated to a dropwise addition of the Grignard reagent (while the temperature was maintained below 5° C.). Upon addition the reaction mixture was stirred at room temperature for about 24 hours. The reaction was monitored for completion by HPLC. The resulting mixture was quenched by pouring into ice-water and extracted with TBME (800 mL×3).

The organic solvents were removed under vacuum and the resulting oil was partitioned into heptane (700 mL) and 1N HCl (700 mL). The two phase mixture was vigorously stirred for about 30 minutes before the layers were separated and the organic layer washed with 1N HCl. The combined acid layers were neutralized with 6N NaOH to about pH 6 and with solid sodium bicarbonate to about pH 8. This aqueous layer was extracted with methylene chloride (400 mL×5) and the combined organic layers were dried (MgSO₄). The volatile solvents were removed under vacuo to yield 48.9 g of an oil. HPLC assay indicated the yield to be 95% pure 1.1 with an SS:SR ratio (1.1:10.0) of 99:1. Proton NMR indicated the oil to be ≧95% pure 1.1. MS m/z 259.1 (M+1).

EXAMPLE 3

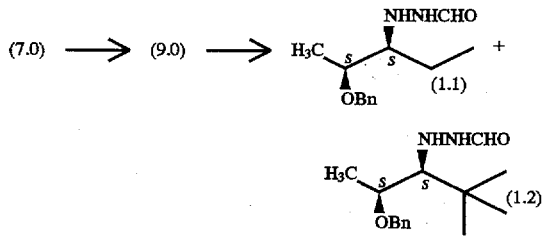

Into a 125 mL round bottom flask equipped with a magnetic stirrer, thermometer and nitrogen bleed was charged 7.0 (2.1 g), TBME (12 mL), triethylamine (1.5 g), and t-butyl-dimethylsilyl chloride (1.7 g). This mixture was stirred overnight at room temperature and HPLC showed that no starting material (7.0) remained. In preparation for the next step, the solution of 9.0 was filtered to remove triethylamine hydrochloride salt.

In a separate 125 mL round bottom flask equipped with a magnetic stirrer, thermometer and nitrogen bleed, was charged EtMgCl (12 mL, 24 mmol, 2.0M in THF) and t-BuMgCl (24 mL, 24 mmol, 1.0M in THF). The resulting solution was stirred for 5 minutes at room temperature and then transferred dropwise to the filtered solution of 9.0. The rate of addition was controlled to maintain a temperature of about 10° C. The solution was then warmed to room temperature and stirred overnight, after which HPLC analysis showed that less than 5% starting material (9.0) remained. The mixture was poured into ice (50 g) containing concentrated HCl (10 g, 12N) and the layers separated. The water layer was washed with methyl t-butyl ether (3×50 mL). The combined organic layers were concentrated to an oil under high vacuum with a rotary evaporator using a bath temperature of about 50° C. The residual oil was dissolved in heptane (20 mL) and extracted with 1N HCl (2×20 mL). The combined water layers were brought to a pH of 6 with 1N NaOH and extracted with methyl t-butyl ether (3×50 mL). The solution was concentrated to an oil to yield 1.26 g. HPLC analysis revealed the oil to be a mixture of products 1.1 and 1.2 in a ratio of 95:5 (1.1:1.2).

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A process for producing a hydrazide of the formula:

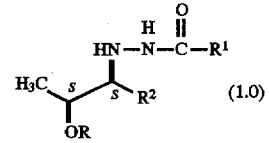

comprising reacting a hydrazone of the formula:

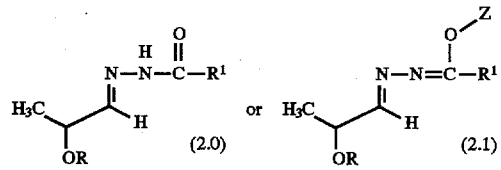

wherein said hydrazone is in toluene, with a mixture of Grignard reagents, wherein said Grignard reagents are in a suitable organic solvent; wherein:

(A) Z is a suitable carbonyl protecting group;

(B) R is a suitable —OH protecting group;

(C) $R^1$ is selected from: (1) H; (2) a non-enolizable alkyl; (3) a non-enolizable substituted alkyl; (4) aryl; (5) substituted aryl; (6) —S-aryl; (7) —S-(substituted aryl); (8) —S-alkyl; (9) —S-(substituted alkyl); (10) alkoxy; (11) substituted alkoxy; (12) aryloxy; or (13) substituted aryloxy;

(D) said mixture of Grignard reagents comprises $R^2$MgX in admixture with $R^3$MgX;

(E) $R^2$ is a suitable alkyl, substituted alkyl, alkenyl, alkynyl, aryl, substituted aryl, or aralkyl group capable of adding to the —C=N group of the hydrazone to produce the hydrazide;

(F) $R^3$ is a suitable alkyl, substituted alkyl, aryl or substituted aryl group that is more sterically hindered than said $R^2$ group;

(G) X is independently selected from Cl, Br or I for each Grignard reagent;

(H) when said hydrazone is a compound of Formula 2.0 then the reaction is conducted at a temperature of about +30° to about −40° C.; and (I) when said hydrazone is a compound of Formula 2.1 then the reaction is conducted at a temperature of about +40° to about −20° C.

2. The process of claim 1 wherein Z is TBDMS.

3. The process of claim 1 wherein R is benzyl.

4. The process of claim 1 wherein $R^1$ is H or $-OC(CH_3)_3$.

5. The process of claim 1 wherein $R^2$ is a 1° alkyl group and $R^3$ is a 3° alkyl group, and X is Cl or Br.

6. The process of claim 5 wherein $R^2$ is ethyl and $R^3$ is t-butyl, and X is Cl or Br.

7. The process of claim 6 wherein X is Cl.

8. The process of claim 1 wherein said hydrazone is a compound of Formula 2.1, said $R^2MgX$ Grignard reagent is used in mounts of about 1.0 to about 2.0 eq, and said $R^3MgX$ Grignard reagent is used in an amount that is about 1 to 2 times the amount of said $R^2MgX$ Grignard reagent.

9. The process of claim 8 wherein the reaction is conducted at about 0° to about 25° C.

10. The process of claim 1 wherein said hydrazone is a compound of Formula 2.0, said $R^2MgX$ Grignard reagent is used in amounts of about 1.0 to about 4.0 eq, and said $R^3MgX$ Grignard reagent is used in an amount that is about 1 to 2 times the amount of said $R^2MgX$ Grignard reagent.

11. The process of claim 10 wherein R is benzyl and $R^1$ is H or $-OC(CH_3)_3$.

12. The process of claim 11 wherein the reaction temperature is about 0° to about −15° C.

13. The process of claim 1 wherein said organic solvent is selected from: toluene or diethyl ether.

14. The process of claim 1 wherein Z is TBDMS; R is benzyl; $R^1$ is H or $-OC(CH_3)_3$; $R^2$ is a 1° alkyl; $R^3$ is a 3° alkyl; and X is Cl or Br.

15. The process of claim 14 wherein the hydrazone is a compound of Formula 2.1, said $R^2MgX$ Grignard reagent is used in amounts of about 1.0 to about 2.0 eq, and said $R^3MgX$ Grignard reagent is used in an amount that is about 1 to 2 times the amount of said $R^2MgX$ Grignard reagent.

16. The process of claim 15 wherein $R^1$ is H; $R^2$ is ethyl; and $R^3$ is t-butyl.

17. The process of claim 16 wherein said reaction temperature is about 0° to about 25° C., and said solvent is toluene.

18. The process of claim 14 wherein the hydrazone is a compound of Formula 2.0, said $R^2MgX$ Grignard reagent is used in amounts of about 1.0 to about 4.0 eq, and said $R^3MgX$ Grignard reagent is used in an amount that is about 1 to 2 times the amount of said $R^2MgX$ Grignard reagent.

19. The process of claim 18 wherein $R^1$ is $-OC(CH_3)_3$; $R^2$ is ethyl; and $R_3$ is t-butyl.

20. The process of claim 17 wherein said reaction temperature is about 0° to about −15° C., and said solvent is toluene.

* * * * *